(12) United States Patent
Nieto (10) Patent No.: US 8,765,717 B2
(45) Date of Patent: Jul. 1, 2014

(54) MELOXICAM AND GLUCOSAMINE FORMULATION AND USES THEREOF

(75) Inventor: Jorge D. Nieto, Munro (AR)

(73) Assignee: Monte Verde S.A., San Juan (AR)

( * ) Notice: Subject to any disclaimer, the term of this patent is extended or adjusted under 35 U.S.C. 154(b) by 551 days.

(21) Appl. No.: 12/496,999

(22) Filed: Jul. 2, 2009

(65) Prior Publication Data

US 2010/0004200 A1    Jan. 7, 2010

(30) Foreign Application Priority Data

Jul. 3, 2008    (AR) ............................... P080102880

(51) Int. Cl.
*A61K 31/5415* (2006.01)
*A61K 31/7008* (2006.01)

(52) U.S. Cl.
USPC ........................................ 514/62; 514/226.5

(58) Field of Classification Search
None
See application file for complete search history.

(56) References Cited

U.S. PATENT DOCUMENTS 4,962,091 A    10/1990    Eppstein et al.

FOREIGN PATENT DOCUMENTS

| WO | WO-94/07529 | | 4/1994 |
|---|---|---|---|
| WO | WO 02/26239 | * | 4/2002 |
| WO | WO 2008/120965 | * | 10/2008 |

OTHER PUBLICATIONS de Hooge, A. et al "Male IL-6 gene knock out mice . . . " Osteoarthritis and Cartilage (2005) vol. 13, pp. 66-73.*
McGeough, M. et al "Cutting edge: IL-6 is a marker of inflammation . . . " (2012) vol. 189, pp. 2707-2711.*
Lequesne, M. G, et al., "Indexes of severity for osteoarthritis of the hip and knee. Validation—value in comparison with other assessment tests.", Scand J Rheumatol Suppl., 65, (1987), 85-9.
Lequesne, M., "Indices of severity and disease activity for osteoarthritis.", Semin Arthritis Rheum., 20(6 Suppl 2), (Jun. 1991), 48-54.
Mezei, Tibor, et al., "Manufacture of High-Purity Meloxicam via Its Novel Potassium Salt Monohydrate", Org. Process Res. Dev.,13(3), (2009), 567-572.
Ogino, K., et al., "Meloxicam inhibits prostaglandin E(2) generation via cyclooxygenase 2 in the inflammatory site but not that via cyclooxygenase 1 in the stomach.", Pharmacology, 61(4), (Nov. 2000), 244-50.

* cited by examiner

*Primary Examiner* — Leigh Maier
(74) *Attorney, Agent, or Firm* — Schwegman, Lundberg & Woessner, P.A.

(57) ABSTRACT

Provided herein is a process for making compositions and methods of using such compositions to treat pain, inflammation and/or inflammatory disease or disorder including degenerative osteoarticular disease.

14 Claims, 4 Drawing Sheets

MELOXICAM AND GLUCOSAMINE FORMULATION AND USES THEREOF

PRIORITY

This application claims benefit of the filing date of Argentina Application Ser. No. P 2008 0102880, filed Jul. 3, 2008, the contents of which are specifically incorporated herein by reference.

BACKGROUND

Degenerative osteoarticular diseases are chronic joint diseases, especially those having great movement, which often occur due to the wear or damage of the joint surfaces; however, they can also have traumatic, autoimmune and other causes. Of these diseases, the most predominant is osteoarthritis, which is estimated to affect about 1% of the population under 30 years of age, about 10% of the population at the age of 40 and more than 50% of the population over the age of 50. The occurrence of this pathology is higher in adults between 50 and 60 years of age, especially in women above 55 years of age, osteoarthritis being most common in knees and hands in women and in hips in men.

The risk factors that contribute to the development this disease are being above 45 years of age, female, having a genetic predisposition to suffer form this disease, working with mechanical forces that compromise joints (e.g., workers who carry heavy burdens), the excessive use of joints (e.g., sportsmen), a history of joint trauma, having suffered from joint diseases previously (e.g. rheumatoid arthritis, gout, etc.) and obesity.

At the beginning, osteoarthritis can progress without any pain, but after a time it causes stiffness, progressive movement limitations, deformation due to the swelling of the affected joints and chronic pain in the affected areas with sporadic acute events.

Osteoarthritis can be classified into different degrees, according to the characteristics of the affected joint:

| Kellgren & Lawrence Radiographic Grading | |
| --- | --- |
| Grade I - doubtful OA | Doubtful osteophytes |
| | Normal joint space |
| Grade II - minimum OA | Definite osteophytes |
| | Possible narrowing of joint space |
| Grade III - moderate OA | Multiple osteophytes |
| | Defined narrowing of joint space |
| | Subchondral bone sclerosis |
| Grade IV - severe OA | Very big osteophytes |
| | Severe narrowing of joint space |
| | Marked bone sclerosis |
| | Bone cysts |
| | Deformation or eating disorders |

There are many types of treatment for osteoarthritis; however, these treatment are not always effective and many of them result in adverse side effects.

SUMMARY

This instant invention provides a process for making compositions and methods of using such compositions to treat pain and/or inflammatory diseases or disorders, such as degenerative osteoarticular diseases, including, but not limited to, osteoarthritis (a degenerative form of arthritis) and rheumatoid arthritis.

One embodiment provides a method to prepare an oral pharmaceutical composition comprising glucosamine and meloxicam, the method comprising wet granulation of glucosamine and meloxicam using a polar solvent and a binder up to about 20% w/w of the final composition. In one embodiment, the solvent and binder comprise up to about 15% w/w of the total composition.

In one embodiment, the solvent is acetic acid, butanol, isopropanol, propanol, ethanol, methanol, formic acid or combinations thereof. In another embodiment, the acetic acid, butanol, isopropanol, propanol, ethanol, methanol, formic acid or combinations thereof with and without water. In one embodiment, the solvent is ethanol or ethanol and water.

In another embodiment, the binder is lactose powder, dibasic calcium phosphate, sucrose, corn (maize) starch, microcrystalline cellulose, modified cellulose or povidone. In one embodiment, the binder is povidone.

In one embodiment, the solvent is ethanol and the binder is povidone.

Another embodiment provides a method to prepare a pharmaceutical composition (e.g., an oral composition) comprising glucosamine and meloxicam comprising: a) combining glucosamine, meloxicam, polyethylene glycol and a surfactant; b) dissolving a binder in a polar solvent, wherein the binder and polar solvent comprise up to about 20% w/w of the total composition; c) combining the solution obtained in b) to the mixture obtained in a) and mixing until a homogeneous mixture is obtained; and d) drying the mixture obtained in c) for up to about two hours at a temperature up to about 40° C. In one embodiment, the surfactant is sodium lauryl sulphate or polysorbate. In another embodiment, the solvent is ethanol, isopropanol or a mixture of water and ethanol.

One embodiment provides a method to treat pain and/or inflammatory disease or disorder, such as degenerative osteoarticular disease, comprising administering an effective amount of glucosamine or a pharmaceutically acceptable salt thereof and meloxicam or a pharmaceutically acceptable salt or ester thereof to a subject in need thereof so as to treat said pain and/or inflammatory disease or disorder, including degenerative osteoarticular disease (with or without inflammation). In one embodiment the glucosamine is glucosamine sulphate. In another embodiment, the glucosamine and meloxicam are administered together in the same pharmaceutical composition. In another embodiment, the osteoarticular disease is osteoarthritis. In one embodiment, the glucosamine/meloxicam composition administered to a subject is prepared by the methods described herein.

DETAILED DESCRIPTION

This instant invention provides a process for making compositions comprising glucosamine and meloxicam and meth- ods of using such compositions to treat pain and/or inflammation, such as inflammatory disease or disorders including degenerative osteoarticular diseases, including, but not limited to, osteoarthritis (a degenerative form of arthritis) and rheumatoid arthritis. In one embodiment, the oral (e.g., solid) pharmaceutical compositions comprising glucosamine and meloxicam are prepared by wet granulation, wherein the granulation solution (e.g., ethanol and povidone) is added in a ratio of up to about 20% w/w of the total formulation (e.g., up to about 20 g of povidone/ethanol solution for about 100 g of total final composition). In one embodiment, the glucosamine and meloxicam are present in a single pharmaceutical composition. In another embodiment, the glucosamine and meloxicam are in separate pharmaceutical compositions. They can be administered simultaneously or sequentially.

As used herein "glucosamine" refers to 2-amin-2 desoxy-alpha-D-glucose and salts thereof (e.g., glucosamine sulphate). Structure-wise, glucosamine is a glucose modified with an amino group replacing the hydroxyl group on carbon 2.

Glucosamine can be isolated and purified from natural sources, purchased from commercial suppliers or synthesized by any method suitable for the synthesis of pharmaceutically acceptable glucosamine. Glucosamine includes, but is not limited to, glucosamine; glucosamine salts of hydrochloric, iodic, sulfuric, phosphoric, or other pharmaceutically acceptable acid; glucosamine-2-sulfate; glucosamine-3-sulfate; glucosamine-6-sulfate; glucosamine-2,3-disulfate; glucosamine-2,6-disulfate; glucosamine-3,6-disulfate; glucosamine-3,4,6-trisulfate; glucosamine pentaacetate; glucosamine-1-phosphate; glucosamine-6-phosphate; N-acetylglucosamine-6-phosphate; N-acetylglucosamine-1-phosphate; N-acetyl-D-glucosamine; and uridine diphosphate (UDP)-N-acetylglucosamine.

Glucosamine is found in many body tissues and secretions. This amino sugar works as a substrate for the biosynthesis of macromolecules, such as chondroitin sulphate and hyaluronic acid, which aid in the formation of collagen. A local absence of glucosamine has been reported in arthritis, possibly due to the alteration in the permeability of the articular capsule and enzymatic alterations in the synovial membrane and cartilage cells. An exogenous supply of glucosamine sulphate can be used in order to restore the endogenous lack of said substance. Once inside the body, glucosamine sulphate is dissociated into a sulphate ion and a D-glucosamine ion (molecular weight=179.17). At 37° C., glucosamine has a pKa of 6.91 and is believed to be absorbed by the small intestine and pass through other biological barriers.

As used herein, meloxicam refers to (8E)-8-[hydroxy-[(5-methyl-1,3-thiazol-2-yl)amino]methylidene]-9-methyl-10,10-dioxo-10λ$^6$-thia-9-azabicyclo[4.4.0]deca-1,3,5-trien-7-one and has the following structure:

Meloxicam, an enolic derivative, is a nonsteroidal anti-inflammatory drug of the oxicam class. It inhibits the synthesis of prostaglandins, which are mediators of inflammation.

Clinical trials have shown that the occurrence of adverse gastrointestinal events such as bleeding, perforation or ulcers is less frequent in patients treated with meloxicam than with other nonsteroidal anti-inflammatory drugs. Additionally, in an animal model suffering from arthritis, meloxicam was reported to cause a higher therapeutic index than other non-steroidal anti-inflammatory drugs, for it can more efficiently inhibit the synthesis of prostaglandins in the inflammation site (Ogino et al., Pharmacology 2000; 61:244-250). On the other hand, meloxicam does not appear to act on other organs (e.g., kidney or gastric mucosa) for it selectively inhibits COX-2 over COX-1.

Both glucosamine and meloxicam are not limited to the salts and the forms disclosed in the specific embodiments of the present invention, but encompass all their pharmaceutically accepted esters, ethers, salts and polymorphs.

In addition to the active pharmaceutical agent, the compositions can include several inactive ingredients or excipients, including, but not limited to, binders, fillers, lubricants, and disintegrants. For example, the compositions disclosed herein can include diluents between about 20-80% w/w, moisturizers or wetting agents between about 2-10% w/w, surface active agents (e.g., surfactants) between about 0.5-5.0% w/w, acidifying agents between about 0.5-5.0% w/w, sweeteners between about 0.1-5.0% w/w, flavourings between about 0.2-5.0% w/w, binders (e.g., Povidone K30) between about 0.5-10% w/w, glidants (flow aids; e.g., colloidal silicon dioxide) between about 0.5-2.0% w/w, lubricants between about 5-15% w/w (including, for example, anti-adherents and glidants), and disintegrants between about 0.5-20% w/w.

As used herein, "polar solvent," "organic polar solvent," "polar granulation solvent" or "polar agglutination solvent" includes, but is not limited to, acetic acid, butanol, isopropanol, propanol, ethanol, methanol, formic acid, water and combinations thereof. For example, in one embodiment, the polar solvent is ethanol.

A "binder" refers to an excipient added to help hold a tablet together and give it strength. A wide variety of binders may be used, including, but are not limited to, lactose powder, dibasic calcium phosphate, sucrose, corn (maize) starch, microcrystalline cellulose and modified cellulose (for example hydroxymethyl cellulose). In one embodiment, the binder is povidone (e.g., Povidone K30; povidone is polyvinyl pyrrolidone (PVP). As PVP is not soluble in water, a solvent is used to carry PVP in a liquid.

A disintegrant generally aids in disintegration of, for example, a tablet after it is ingested. For example, many disintegrants are added to ensure that the tablet breaks up in the digestive tract. In many cases they hydrate readily in water to aid tablet dispersion once swallowed, releasing the API for absorption. Some binders, such as starch and cellulose, are also excellent disintegrants.

Lubricants can also be added to the pharmaceutical compositions. Lubricants include, for example, magnesium stearate; stearic acid (stearin), hydrogenated oil, and sodium stearyl fumarate. These help the tablets, once pressed, to be more easily ejected from the die.

A "subject" is a vertebrate, including a mammal, such as a human. Mammals include, but are not limited to, humans, farm animals, sport animals, and pets.

As used herein, "treat" or "treating" includes treating, preventing, ameliorating, or inhibiting a disease, disorder and/or a symptom of a disease and/or a disorder of an organism.

As used herein, an "effective amount" generally means a sufficient amount of a compound to provide the desired local or systemic effect and performance.

The phrase "same pharmaceutical composition" refers to the fact that the active principles, glucosamine and meloxicam, are present in the pharmaceutical composition in one single dosage unit.

The phrase "pharmaceutically acceptable" means a carrier, diluent, excipient, and/or salt that is compatible with the other ingredients of the formulation, and not deleterious to the recipient thereof.

As used herein, "pharmaceutically acceptable carrier" refers to carrier materials without significant pharmacological activity at the quantities used that are suitable for administration with other compounds, and include any such materials known in the art, e.g., any liquid, gel, solvent, liquid diluents, solubilizer, microspheres, liposomes, microparticles, lipid complexes, or the like, that is sufficiently nontoxic at the quantities employed and does not interact with the drug to be administered in a deleterious manner. Examples of suitable carriers for use herein include water, buffers, mineral oil, silicone, inorganic or organic gels, aqueous emulsions, liquid sugars, lipids, microparticles, waxes, petroleum jelly, and a variety of other oils and polymeric materials.

It is noted that, as used herein the singular forms "a," "an," and "the" include plural referents unless the context clearly dictates otherwise. Thus, as used herein, the singular form may be used interchangeably with the plural form, and vice versa.

As used herein, "including" or "includes" or the like means including, without limitation.

Use, Administration and Preparation of Compositions

In one embodiment, the compositions disclosed herein are used to treat pain and/or inflammation, such as inflammatory disease or disorder including degenerative osteoarticular diseases, including, but not limited to, osteoarthritis (a degenerative form of arthritis) and rheumatoid arthritis. The treatment of pain, inflammation or inflammatory disease or disorder refers to the treatment of any pain, inflammation or inflammatory disease or disorder or a symptom thereof including, but not limited to, osteoarthritis, arthritis, spondyloarthopathies, gouty arthritis, juvenile arthritis, autoinflammatory diseases (lupus), crystal arthritis, capsulitis, tendonitis, ligamentitis, traumatic joint injury, rheumatoid arthritis, gastrointestinal disorders (such as inflammatory bowel disease, gastric ulcer, Crohn's disease, gastritis, irritable bowel syndrome, ulcerative colitis), skin disorders (such as psoriasis, eczema, burns or dermatitis), headache (migraine, sinus or, tension), or other pain or inflammatory disorders, including injuries or wounds, surgery or dental pain.

A surprising and unexpected aspect of this invention is the use of the combination of glucosamine and meloxicam active principles, in the same pharmaceutical composition for the treatment of pain and/or inflammation, such as inflammatory disease or disorder including degenerative osteoarticular diseases. Shown herein is the surprising discovering that the combination of glucosamine and meloxicam acts synergistically to ease pain in the acute phases of osteoarticular diseases and in movement of the affected joint in the short and medium term.

The present invention has further demonstrated that the combination of the glucosamine and meloxicam causes an apparent decrease in the side effects compared to the drugs administered alone. In one embodiment, the compositions of the invention do not include cetyl myristoleate (CMO) and related compounds (e.g., esters of an unsaturated fatty acid (e.g., having cis double bonds, having 12 or more carbon atoms, or palmitoleic acid, oleic acid, linoleic acid, arachidonic acid, or nervonic acid etc.) and an alcohol (e.g., long chain including those alcohols having 10 or more carob atoms that can be linear or branched)). In another embodiment, the compositions of the invention do not include a tetracycline compound.

As to the preparation of oral formulations, provided herein is a formulation process which combines glucosamine and meloxicam to achieve a formulation which has superior stability, solubility and homogeneity characteristics.

As the active ingredient in the formulation represents a small portion of the overall tablet, the challenge was to ensure that each tablet has the same amount of the active ingredient. Sometimes, blending the ingredients is not enough. For example, the active ingredient can segregate from the other ingredients in the blending process. The ingredients may be incompatible because of particle size, particle density, flow characteristics, compressibility and moisture content. These incompatibilities can cause problems such as segregations during blending or during transfer of the product to the press as well as separation of the active on the tablet press. One solution is granulation. The granulation process combines one or more powders and forms a granule. Wet granulation refers to the process of adding a liquid to powders. The liquid can be either aqueous based or solvent based. In general, aqueous liquids have the advantage of being safer to deal with than solvents. However, some granulation processes are not compatible with water. In these instances, a liquid that includes a binder is used.

In one embodiment, the method to prepare an oral pharmaceutical composition that contains the active principles of glucosamine and meloxicam is as follows: a) combine glucosamine, meloxicam, polyethylene glycol and a surface acting agent; b) dissolve a binder in a polar solvent, wherein the binder and polar solvent comprise up to about 20% w/w of the total composition; c) combine the solution obtained in b) to the mixture obtained in a) and mix until a homogeneous mixture is obtained; and d) dry the mixture obtained in c) for up to about two hours at a temperature up to about 40° C.

Under these processing conditions, a homogeneous (e.g., a mixture that is similar throughout) and physicochemically stable product during the entire intended shelf life is obtained.

The use of said combination is not limited to oral solid compositions, other administration forms can be included, such as oral liquid compositions, parenteral compositions (intravenous, intramuscular and intraperitoneal), rectal, topical, dermal, and transdermal compositions. In some embodiments, the compositions of the invention are administered locally (topically, injected or placed surgically) to pain and/or inflammation, such as inflammatory disease or disorder locations, including degenerative osteoarticular disease locations.

The therapeutic agents can be formulated for sustained release (for example, using microencapsulation, see WO94/07529, and U.S. Pat. No. 4,962,091). The total active ingredients in such formulations comprise from 0.001 to 99.9% by weight of the formulation. The formulations can, where appropriate, be conveniently presented in discrete unit dosage forms and can be prepared by any of the methods available to the pharmaceutical arts. Such methods may include the step of mixing the therapeutic agents with liquid carriers, solid matrices, semi-solid carriers, finely divided solid carriers or combinations thereof, and then, if necessary, introducing or shaping the product into the desired delivery system.

When the therapeutic agents of the invention are prepared for oral administration, they are generally combined with a pharmaceutically acceptable carrier, diluent or excipient to form a pharmaceutical formulation, or unit dosage form. For oral administration, the therapeutic agents can be present as a powder, a granular formulation, a solution, a suspension, an emulsion or in a natural or synthetic polymer or resin for ingestion of the active ingredients from a chewing gum. The therapeutic agents can also be presented as a bolus, electuary or paste.

Pharmaceutical compositions containing the therapeutic agents of the invention can be prepared by procedures available to the art. For example, the therapeutic agents can be formulated with excipients, diluents, or carriers, and formed into tablets, capsules, solutions, suspensions, powders, aerosols and the like. Examples of excipients, diluents, and carriers that are suitable for such formulations include water, buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included, such as paraffin. Resorption accelerators such as quaternary ammonium compounds can also be included. Surface active agents, such as sodium laurel sulphate, polysorbates cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For example, tablets or caplets containing the therapeutic agents of the invention can include buffering agents, such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more therapeutic agents of the invention are designed to resist disintegration in the stomach and dissolve in the more neutral to alkaline environment of the duodenum. For example, the formulations can be so constituted that they release the therapeutic agents, for example, in a particular part of the intestinal, possibly over a period of time. Coatings, envelopes, and protective matrices may be made, for example, from polymeric substances, such as polylactideglycolates, liposomes, microemulsions, microparticles, nanoparticles, or waxes.

The compositions can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic agents of the invention can also take the form of an aqueous or anhydrous solution or dispersion, or alternatively the form of an emulsion or suspension or salve.

Thus, the compositions can be formulated for parenteral administration (e.g., by injection, for example, bolus injection or continuous infusion) and may be presented in unit dose form in ampoules, pre-filled syringes, small volume infusion containers or in multi-dose containers. As noted above, preservatives can be added to help maintain the shelve life of the dosage form. The compositions with optional other ingredients can form suspensions, solutions, or emulsions in oily or aqueous vehicles, and can contain formulatory agents such as suspending, stabilizing and/or dispersing agents. Alternatively, the compositions with optional other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers, polyglycols and polyethylene glycols, $C_1$-$C_4$ alkyl esters of short-chain acids, ethyl or isopropyl lactate, fatty acid triglycerides, isopropyl myristate, animal, mineral and vegetable oils and polysiloxanes.

It is possible to add, if desired, additional ingredients chosen from antioxidants, surfactants, other preservatives, film-forming, keratolytic or comedolytic agents, perfumes, sweetners, flavorings and colorings.

It should be understood that in addition to the ingredients particularly mentioned above the formulations of this invention may include other agents conventional in the art having regard to the type of formulation in question.

The compositions of the present invention can be in defined dosage units, e.g., in the form of a single dose, in multiple doses, in a continuous or intermittent manner, depending, for example, upon the recipient's physiological condition, whether the purpose of the administration is therapeutic or prophylactic, and other factors known to skilled practitioners. One formulation of a single dose contains between about 100 and about 3,000 mg of glucosamine or a pharmaceutically acceptable salt thereof and between about 0.1 and about 15 mg of meloxicam or a pharmaceutically acceptable salt or ester thereof. The amount of active principles in the pharmaceutical composition will vary according to the administration route, the nature of the treatment for the condition and the age, weight and state of the patient. The present invention provides advantageous dosing consisting of one dose per day which provides the added benefit of increased patient compliance. Such dosing in useful in the acute and chronic phase of pain and/or inflammation, such as inflammatory disease or disorder including degenerative osteoarticular disease.

Numerous modifications and variations of the presently disclosed subject matter are possible in light of the above teachings. It is therefore to be understood that within the scope of the appended claims, the disclosed subject matter may be practiced otherwise than as specifically described herein.

The presently disclosed subject matter may be illustrated by the following non-limiting examples.

EXAMPLES

Example 1

The following example describes the pharmaceutical formulation in pouches, as well as the method for obtaining a batch of 1,000 pouches of the formulation.

By way of clarification, the example of the formulation is solely illustrative and is not intended to limit the present invention. Thus, even though the formulation of Example 1 illustrates a pouch containing 1,500 milligrams of glucosamine sulphate and 15 milligrams of meloxicam, other pharmaceutical forms of administration, such as capsules and tablets, with other amounts or forms of said active principles may be included in the present invention. Similarly, excipients or vehicles other than those mentioned in this example may likewise fall within the scope hereof.

For example, in one embodiment, the pharmaceutical compositions are in the form of bags or capsules, wherein each single dose of said pharmaceutical composition comprises 1.500 mg or 750 mg of glucosamine sulphate and 15 mg or 7.5 mg of meloxicam, depending on whether they are pouches or capsules, respectively, and further comprises, expressed in % by weight, the following agents: diluents between 20-80%, moisturizers or wetting agents between 2-10%, surface active agents (e.g., surfactants) between 0.5-5.0%, acidifying agents between 0.5-5.0% (e.g., weak acids such as citric acid and acetic acid), sweeteners between 0.1-5.0%, flavours between 0.2-5.0%, binder (e.g., Povidone K30) between 0.5-10%, glidants (flow aids; e.g., colloidal silicon dioxide) between 0.5-2.0%, lubricants between 5-15% (including, for example, anti-adherents and glidants), disintegrants between 0.5-20%.

Formula:
Each pouch contains:

| | |
|---|---|
| Glucosamine Sulphate Potassium chloride (equivalent to 1500.00 mg of Glucosamine Sulphate) | 1997.0 mg |
| Meloxicam | 15.0 mg |
| Polyethylene glycol | 60.0 mg |
| Sodium Lauryl Sulphate | 1.0 mg |
| Sorbitol | 1402.0 mg |
| Citric Acid Hydrate | 200.0 mg |
| Sodium Saccharin | 7.0 mg |
| Aspartame | 18.0 mg |
| Lemon essence | 200.0 mg |
| Povidone K30 | 40.0 mg |
| Colloidal Silice Dioxide | 60.0 mg |
| Ethyl Alcohol (it evaporates) | 600.0 mg |

Preparation Method:

20 grams of colloidal silicon dioxide and 15 grams of meloxicam were mixed for two minutes. Thereafter, a part of the glucosamine sulphate (about 700 grams) was mixed with 60 grams of polyethylene glycol, 1 gram of sodium lauryl sulphate, 7 grams of saccharine, 200 grams of citric acid hydrate and the above meloxicam mixture.

The above mixture was then put in a granulator along with 1402 grams of sorbitol and blended. After that, the remainder of the glucosamine sulphate was added to the mixture and it was further blended.

40 grams of Povidone K30 were dissolved in 600 grams of ethanol and were granulated in the granulator with the mixture described above.

Thereafter, said granulation was dried for an hour and a half at between 37° and 40° C. Next, 40 grams of colloidal silice dioxide, the aspartame and the essence were added to the dried granulation.

The final granulation was packed into three-ply bags of dioxide-aluminum-polyethylene paper at theoretical weight.

Example 2

Rats suffering from artificially provoked inflammation of their knees were administered an intra-articular combination of glucosamine and meloxicam or glucosamine or meloxicam separately. The combination of glucosamine and meloxicam resulted in a significant decrease of IL-6 values (Interleukin 6; IL-6 is the cytokine that, among other functions, triggers the activation of osteoclasts, which are in charge of removing bone matrix) regarding the control group, unlike what was observed with the administration of glucosamine or meloxicam separately.

Therefore, the results demonstrate that the combination of glucosamine and meloxicam surprisingly acts synergistically to inhibit the cytokine that acts in bone resorption, and therefore in deforming joints, as occurs in degenerative osteoarticular diseases.

Example 3

Data from a clinical trial with humans is provided herein. The trial was performed with three arms, at random and blind, of patients suffering from different degrees of primary hip or knee arthritis (I, II or III).

The trial consisted in treating patients for 90 days with a single oral dose, who have been sorted at random in three groups: those treated with 1,500 mg of glucosamine sulphate and 15 mg of Meloxicam, those who were only treated with 15 mg of meloxicam and those who were only treated with 1,500 mg of glucosamine sulphate.

Pain and joint function performance was checked every fifteen days by using the pain VAS and the Lequesne algo-functional index of severity. The VAS assesses the pain in the knee by a visual scale of 100 mm with a total of 10 divisions wherein 0 means no pain and 10 means the deepest pain. Lequesne algo-functional index is a questionnaire of 13 questions, 5 of which assess the pain expressed by patients, 2 questions refer to the maximum distance walked and 6 questions assess the difficulty in performing everyday activities. The severity index is given by the addition of the scores obtained in each item, wherein 24 is the maximum possible score. The higher the index, the more severe is the clinical picture.

Figure 1:
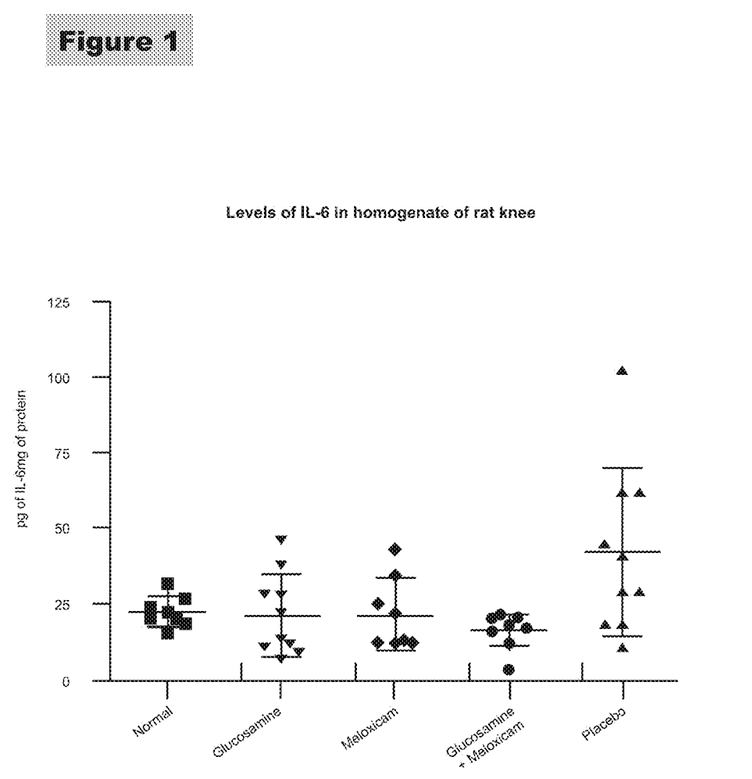
FIG. 1 shows the result of IL-6 levels in a rat knee homogenate after the intra-articular administration of glucosamine, meloxicam, a combination of glucosamine and meloxicam and a placebo (positive control).
Figure 2:
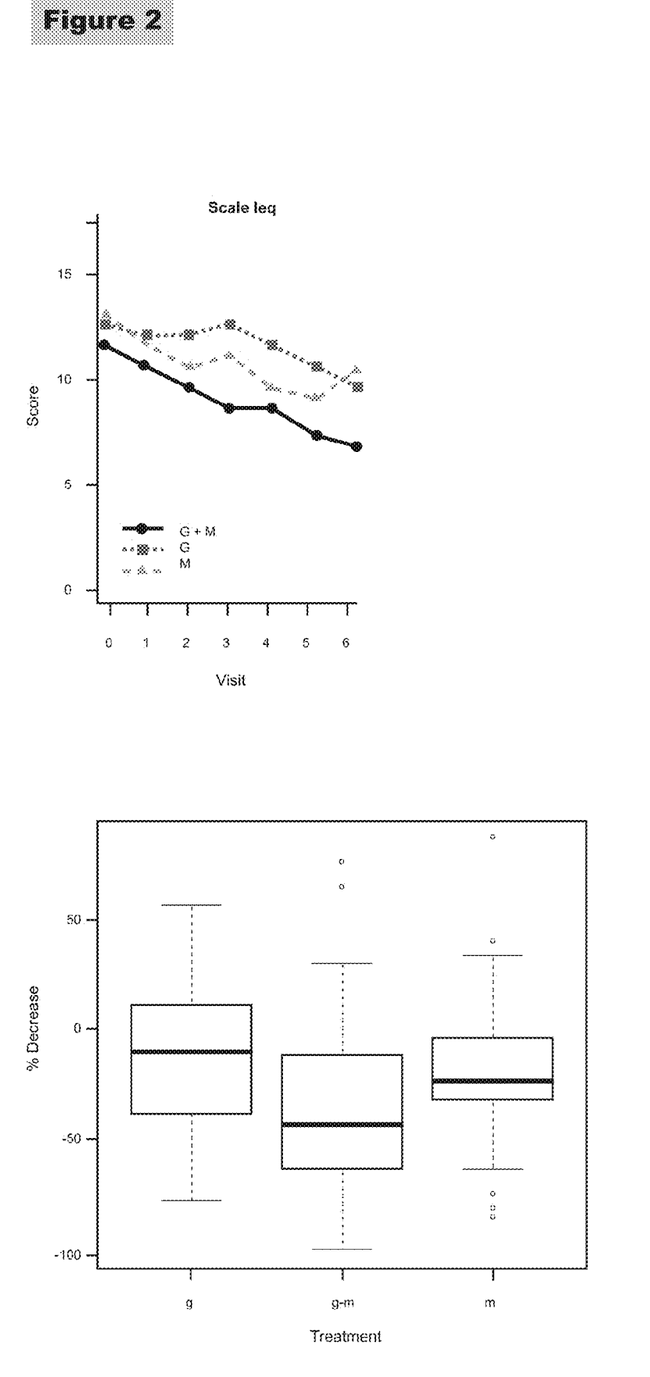
FIG. 2 shows the progress of the Lequesne score measurement (Lequesne, J. Rheumatol. 1997; 24:779-781; Lequesne, Seminars in Arthritis and Rheumatism. 1991; 20(S2):48-54; and Lequesne et al. Scand J. Rheumatology. 1987; S65:85-99) in the 6 visits and at the end of the treatment.

As depicted in FIG. 2, as well as from the trial analysis, Lequesne scale (Algo-functional index) is seen to decrease an average 43% for the group that received a combination of glucosamine and meloxicam, 23% for the group that only received meloxicam and 11% in the group that only received Glucosamine.

Additionally, it is observed that 50% of the patients treated with the combination of glucosamine and meloxicam improved an average of 4 scores in the Lequesne index, as compared to only 3 scores for meloxicam and only 1.5 score for the group that only received glucosamine.

50% of the patients treated with the combination of glucosamine and meloxicam had between a 40% and 100% reduction in the initial value of the Lequesne scale, while the group treated with meloxicam was only able to reduce it between 23% and 85%. The group treated with only glucosamine could only achieve a reduction of 11% to 77% in this index.

25% of the patients showed an enhanced recovery, and the group that received the combination of glucosamine and meloxicam achieved a decrease in the Lequesne scale of 7.5 scores (61%), while in the same proportion, the group that received only meloxicam showed a reduction of 4.5 scores (38%). The reduction achieved by the group of patients who only received glucosamine was of 3.75 scores (32%).

At the end of the three-month treatment period, the average improvement percentage in the Lequesne algo-functional index for the treatment with the combination of drugs was 4.05 times higher than that resulting from administering only glucosamine and 1.86 times higher than that obtained with only meloxicam treatment.

These findings correspond to the studies presented in Example 2 which showed a reduction in IL-6 levels with the glucosamine+meloxicam combination, in comparison to the components administered individually.

Figure 3:
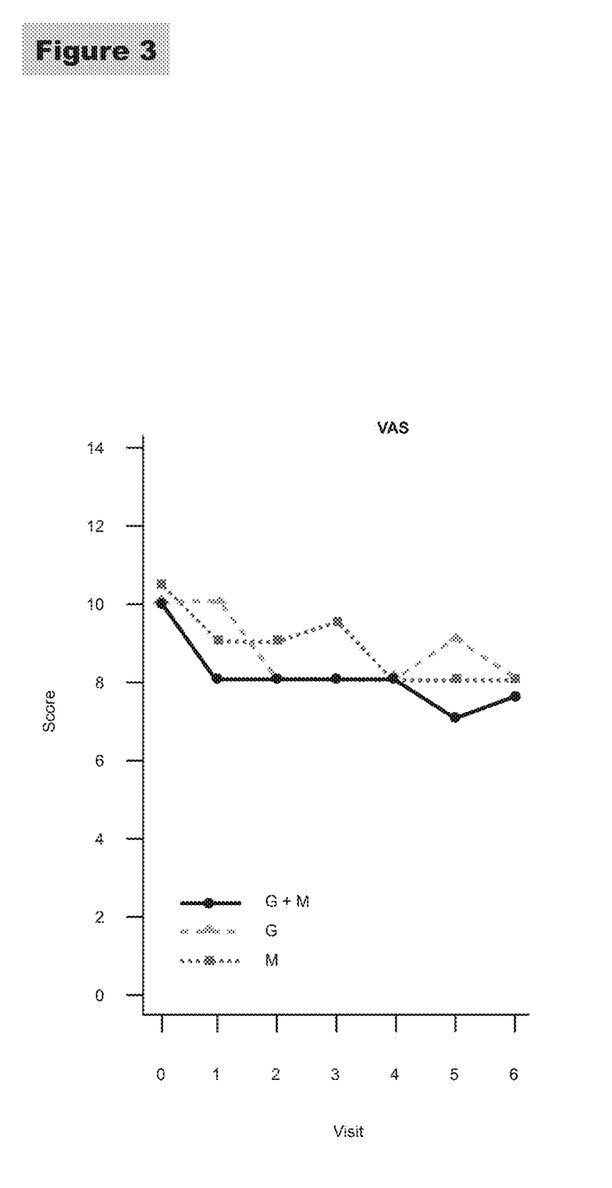
FIG. 3 shows the progress of the VAS scale measurement (Visual Analog pain Scale; a visual analog scale for pain is a straight line with one end meaning no pain and the other end meaning the worst pain imaginable).

FIG. 3 demonstrates that according to the VAS the three groups revealed a 20% reduction in initial values at the end of the treatment. Said reduction was reached during the first month and was sustained during the remaining observation period.

The VAS value decrease showed the highest reduction 15 days after starting with the treatment (first check-up visit) in both the group that received the combination of glucosamine and meloxicam as well as the group that received only meloxicam. The group that was only treated with Glucosamine showed said reduction values only 30 days after treatment was begun. Therefore, the advantage of combining glucosamine and meloxicam from the beginning was confirmed as to pain relief.

Figure 4:
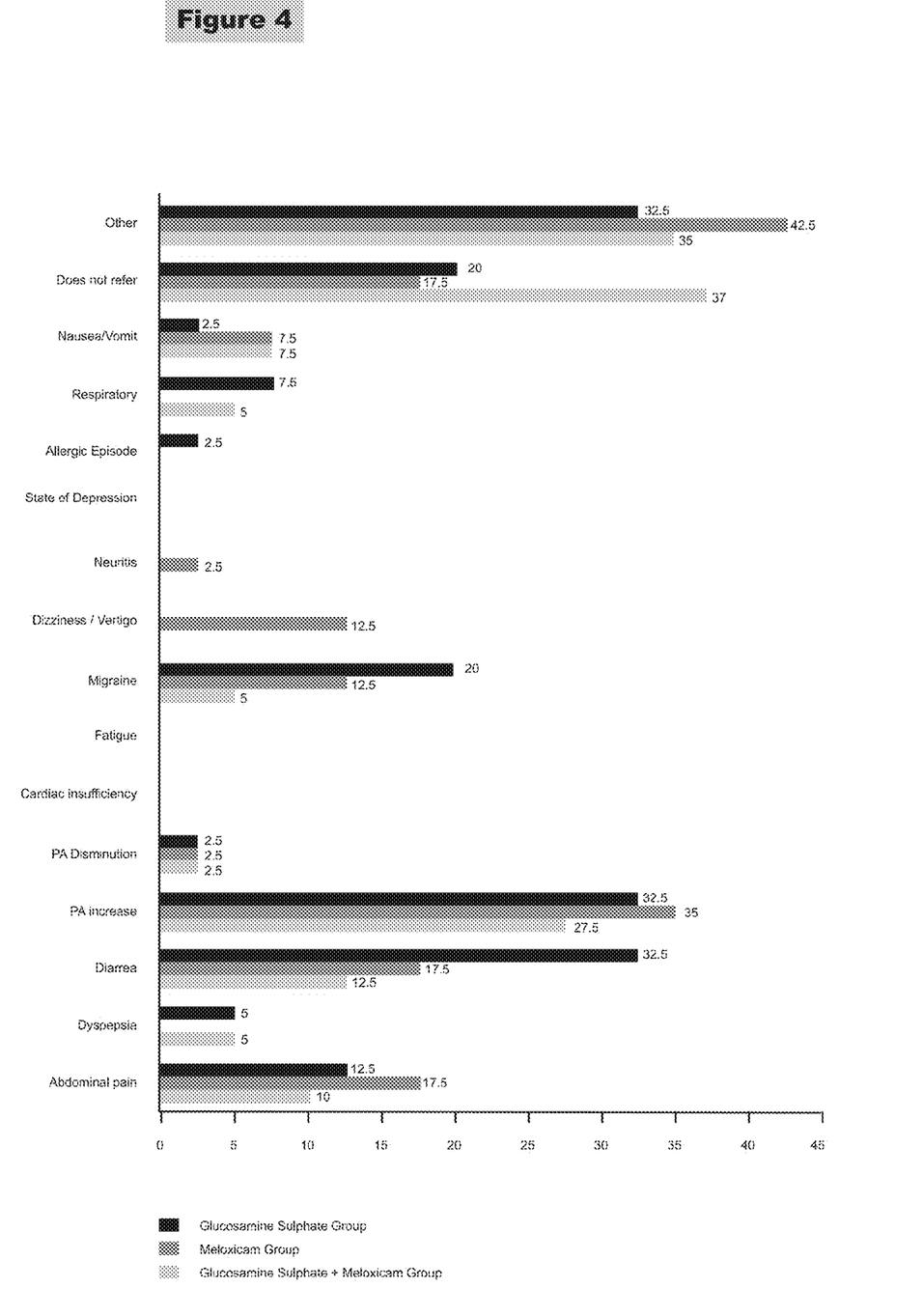
FIG. 4 shows an adverse events table, according to the distribution of patients per assigned medicament.

Finally, FIG. 4 illustrates that the group that received the glucosamine and meloxicam treatment reported a lower side effect index regarding the other groups. In particular, FIG. 4 reveals that the rate of occurrence of adverse gastrointestinal events was lower for the group that received the glucosamine+meloxicam combination.

Any patent, patent document, or reference disclosed herein is incorporated by reference into this disclosed subject matter and forms part of this disclosed subject matter.

What is claimed is:

1. A method to treat degenerative osteoarticular disease, the method comprising administering an effective amount of glucosamine or a pharmaceutically acceptable salt thereof and meloxicam, or a pharmaceutically acceptable salt or ester thereof, in a weight ratio of about 100 parts by weight glucosamine calculated on the basis of the sulfate salt to 1 part by weight meloxicam, to a subject in need thereof so as to treat said degenerative osteoarticular disease.

2. The method of claim 1, wherein glucosamine and meloxicam are administered together in the same pharmaceutical composition.

3. The method of claim 2, wherein the glucosamine and meloxicam are administered once daily.

4. The method of claim 1, wherein glucosamine is glucosamine sulphate.

5. The method of claim 1, wherein the degenerative osteoarticular disease occurs with inflammation.

6. The method of claim 1, wherein the degenerative osteoarticular disease is osteoarthritis.

7. The method of claim 1, wherein the glucosamine or pharmaceutically acceptable salt thereof and the meloxicam, or pharmaceutically acceptable salt or ester thereof are administered together in an oral composition.

8. The method of claim 1, wherein the glucosamine or pharmaceutically acceptable salt thereof and the meloxicam, or pharmaceutically acceptable salt or ester thereof are administered simultaneously.

9. The method of claim 1, wherein the glucosamine or pharmaceutically acceptable salt thereof and the meloxicam, or pharmaceutically acceptable salt or ester thereof are administered sequentially.

10. A method of treating pain comprising administering an effective amount of glucosamine or a pharmaceutically acceptable salt thereof and meloxicam, or a pharmaceutically acceptable salt or ester thereof, in a weight ratio of about 100 parts by weight glucosamine calculated on the basis of the sulfate salt to 1 part by weight meloxicam, to a subject in need thereof so as to treat the pain, wherein the administration is once daily and wherein the pain is associated with a degenerative osteoarticular disease.

11. The method of claim 10, wherein glucosamine is glucosamine sulphate.

12. The method of claim 10, wherein the glucosamine or pharmaceutically acceptable salt thereof and the meloxicam, or pharmaceutically acceptable salt or ester thereof, are administered together in an oral composition.

13. The method of claim 10, wherein the glucosamine or pharmaceutically acceptable salt thereof and the meloxicam, or pharmaceutically acceptable salt or ester thereof, are administered simultaneously.

14. The method of claim 10, wherein the glucosamine or pharmaceutically acceptable salt thereof and the meloxicam, or pharmaceutically acceptable salt or ester thereof, are administered sequentially.

* * * * *